(12) United States Patent
Ramamoorthy et al.

(10) Patent No.: US 12,050,227 B2
(45) Date of Patent: Jul. 30, 2024

(54) LIPID NANODISC FORMATION BY ACRYLOYL-BASED COPOLYMERS

(71) Applicants: THE REGENTS OF THE UNIVERSITY OF MICHIGAN, Ann Arbor, MI (US); NARA INSTITUTE OF SCIENCE AND TECHNOLOGY, Ikoma (JP)

(72) Inventors: Ayyalusamy Ramamoorthy, Ann Arbor, MI (US); Thirupathi Ravula, Ann Arbor, MI (US); Bikash Sahoo, Ann Arbor, MI (US); Kazuma Yasuhara, Ikoma (JP); Jin Arakida, Ikoma (JP); Jun-Ichi Kikuchi, Ikoma (JP)

(73) Assignees: Nara Institute of Science and Technology, Ikoma (JP); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 875 days.

(21) Appl. No.: 16/386,804

(22) Filed: Apr. 17, 2019

(65) Prior Publication Data
US 2019/0346464 A1  Nov. 14, 2019

Related U.S. Application Data

(60) Provisional application No. 62/658,949, filed on Apr. 17, 2018.

(51) Int. Cl.
*G01N 33/92* (2006.01)
*A61K 9/127* (2006.01)
(Continued)

(52) U.S. Cl.
CPC ........... *G01N 33/92* (2013.01); *A61K 9/1273* (2013.01); *C08F 220/14* (2013.01); *G01N 2333/575* (2013.01); *G01N 2405/00* (2013.01)

(58) Field of Classification Search
CPC ................. C08F 220/18; C08F 220/14; C08F 220/1804; C08F 220/34; G01N 33/6842;
(Continued)

(56) References Cited

U.S. PATENT DOCUMENTS 3,888,945 A     6/1975  Arndt et al.
7,452,551 B1 *  11/2008 Unger ................ A61K 47/6925
                                                    424/452

(Continued)

FOREIGN PATENT DOCUMENTS

CN      103665989 A      3/2014
DE      2136585 A1      11/1972
(Continued)

OTHER PUBLICATIONS

Fiori MC, Polymer-encased nanodiscs with improved buffer compatibility, Aug. 7, 2017, Scientific Reports, 7, 7432 . (Year: 2017).*
(Continued)

*Primary Examiner* — Rebecca M Fritchman
(74) *Attorney, Agent, or Firm* — MARSHALL, GERSTEIN & BORUN LLP

(57) ABSTRACT

The disclosure generally relates generally to lipid nanodiscs, in particular to lipid nanodiscs formed from acryloyl-based copolymers. A lipid nanodisc according to the disclosure includes a lipid bilayer having a first hydrophilic face and a second hydrophilic face opposing the first hydrophilic face, and a hydrophobic edge between the opposing hydrophilic faces, and an acryloyl-based copolymer encircling the hydrophobic edge of the lipid bilayer. The acryloyl-based copolymer includes a first monomer unit having a pendant (Continued)

hydrophobic group and a second monomer unit having a pendant hydrophilic group. Methods of making and characterizing the lipid nanodiscs are also disclosed.

19 Claims, 6 Drawing Sheets

(51) Int. Cl.
  *C08F 220/14* (2006.01)
  *C08F 220/18* (2006.01)
(58) Field of Classification Search
  CPC ............. G01N 2333/575; G01N 33/92; G01N 2405/00
  See application file for complete search history.

(56) References Cited

U.S. PATENT DOCUMENTS

| | | | |
|---|---|---|---|
| 8,088,400 | B2 | 1/2012 | Toreki et al. |
| 11,092,605 | B2 | 8/2021 | Ramamoorthy et al. |
| 2009/0117164 | A1 | 5/2009 | Toreki et al. |
| 2012/0128967 | A1 | 5/2012 | Belcher, Jr. et al. |
| 2019/0346464 | A1 | 11/2019 | Ramamoorthy et al. |

FOREIGN PATENT DOCUMENTS

| | | | |
|---|---|---|---|
| DE | 10010851 | A1 | 9/2000 |
| JP | H05092129 | A | 4/1993 |
| JP | H08159998 | A | 6/1996 |
| JP | H11209417 | A | 8/1999 |
| JP | 2004-001240 | A | 1/2004 |
| JP | 4926681 | B2 | 5/2012 |
| JP | 2012-136464 | A | 7/2012 |
| JP | 2012-232287 | A | 11/2012 |
| JP | 2013-020111 | A | 1/2013 |
| JP | 2014-064988 | A | 4/2014 |
| JP | 2014-134573 | A | 7/2014 |
| KR | 2011133264 | | 12/2011 |
| WO | WO-2005/012636 | A1 | 2/2005 |
| WO | WO-2007/024973 | A1 | 3/2007 |
| WO | WO-2008/081995 | A1 | 7/2008 |
| WO | WO-2009/022559 | A1 | 2/2009 |

OTHER PUBLICATIONS

POPOT in "Amphipols, Nanodiscs, and Fluorinated Surfactants: Three Nonconventional Approaches to Studying Membrane Proteins in Aqueous Solutions." (Year: 2010).*
Chen et al., Fabrication of humidity-sensitive polymer films, Dianzi Yuanjian Yu Cailiao, 21(12):24-6 (2002).
De Boos, Non-crosslinking cationic polymers for the shrink-resistant treatment of wool, J. Textile Institute, 75(3):184-90 (1984).
Fefelova et al., Mucoadhesive interactions of amphiphilic cationic copolymers based on [2-(methacryloyloxy)ethyl]trimethylammonium chloride, Int J. Pharm., 339(1-2):25-32 (Jul. 2007).
Kim et al., The design of polymer-based nanocarriers for effective transdermal delivery, Macromol. Biosci., 10(10):1171-6 (Oct. 2010).
Konar et al., Water-soluble quaternary amine polymers as controlled release carrier, J. Appl. Polymer Sci., 69(2):263-9 (1998).
Ozaki et al., Micellar electrokinetic chromatography using high-molecular-mass surfactants: comparison between anionic and cationic surfactants and effects of modifiers, J. Chromatography A, 709(1):3-10 (1995).
Ravula et al., pH Tunable and Divalent Metal Ion Tolerant Polymer Lipid Nanodiscs, Langmuir, 33:10655-62 (2017).
Svec et al., Design of a toolbox for fabrication of analytical microfluidic systems using porous polymer monoliths, pp. 643-645, Micro Total Analysis Systems 2001, Proceedings of the µTAS 2001 Symposium, held in Monterey, CA, USA Oct. 21-25, 2001.
Tada et al., Anti-biofouling properties of polymers with a carboxybetaine moiety, Macromol. Biosci., 9(1):63-70 (Jan. 2009).
Van Wagenen et al., Streaming potential investigations: polymer thin filsm, J. Colloid and Interface Science, 84(1):155-62 (1981).
Yasuhara et al., Spontaneous lipid nanodisc fomation by amphiphilic polymethacrylate copolymers, J. Am. Chem. Soc., 139:18657-63 (2017).
Zhang et al., Synthesis and characterization of resistive-type copolymer humidity sensitive materials, Gongneng Cailiao, 31(Suppl):79-81 (2000).
Hardin et al., Hydrophobic Functionalization of Polyacrylic Acid as a Versatile Platform for the Development of Polymer Lipid Nanodisks, Small, 15(9):e1804813 (2019).
Lee et al., A method for detergent-free isolation of membrane proteins in their local lipid environment, Nat. Protoc., 11(7):1149-62 (Jul. 2016).
Prade et al., A Minimal Functional Complex of Cytochrome P450 and FBD of Cytochrome P450 Reductase in Nanodiscs, Angew Chem. Int. Ed. Engl., 57(28):8458-62 (2018).
Ravula et al., Bioinspired, Size-Tunable Self-Assembly of Polymer-Lipid Bilayer Nanodiscs, Angew. Chem. Int. Ed. Engl., 56(38):11466-70 (Sep. 2017).
Stroud et al., Purification of membrane proteins free from conventional detergents: SMA, new polymers, new opportunities and new insights, Methods, 147:106-17 (Sep. 2018).

* cited by examiner

LIPID NANODISC FORMATION BY ACRYLOYL-BASED COPOLYMERS

CROSS-REFERENCE TO RELATED APPLICATION

The application claims the benefit of U.S. Provisional Application Ser. No. 62/658,949, filed Apr. 17, 2018, the disclosure of which is hereby incorporated by reference in its entirety.

STATEMENT OF GOVERNMENT SUPPORT

This invention was made with government support under grant number AG048934 awarded by the National Institutes of Health. The government has certain rights in the invention.

FIELD OF THE DISCLOSURE

The disclosure relates generally to lipid nanodiscs. In particular, the disclosure relates to lipid nanodiscs formed from acryloyl-based copolymers.

BACKGROUND

Determination of the structure and function of membrane proteins is a challenge due to the difficulty of developing methods of extracting membrane proteins from their native environment, while preserving the correct conformation of the protein in isolation from its native environment. Traditional protocols involve extracting membrane proteins from their native environment using detergents and then including the proteins in a model bilayer system. Unfortunately, the use of detergents leads to issues such as protein inactivation and sample aggregation.

In order to avoid the use of detergents, methods for the isolation, purification, and characterization of membrane proteins have been developed which reconstitute membrane proteins in nanodiscs. Nanodiscs are disc-shaped patches of lipid bilayers surrounded by an amphiphilic belt. Amphiphilic belts that have been used in preparing nanodiscs include different sized membrane scaffold proteins, peptides, and polymers. Membrane scaffold protein-based nanodiscs are good mimics of the membrane; however, the reconstitution of the membrane proteins still require the use of detergents. Additionally, protein-based nanodiscs are restricted to a narrow range of size, difficult to prepare, and expensive to produce. Peptide-based nanodiscs are also limited by several disadvantages, including stability issues, interference from the peptides in biophysical measurements, and are expensive to produce. Similarly, copolymer-based nanodiscs are limited by disadvantages including restricted size range, their non-tolerance in the presence of divalent metal ions and different pH, and are expensive to produce. Thus, a need exists for nanodiscs that can address these difficulties.

SUMMARY

One aspect of the disclosure provides a lipid nanodisc comprising a lipid bilayer comprising a first hydrophilic face and a second hydrophilic face opposing the first hydrophilic face, and a hydrophobic edge between the opposing hydrophilic faces, and an acryloyl-based copolymer encircling the hydrophobic edge of the lipid bilayer, wherein the acryloyl-based copolymer comprises a first monomer unit having a pendant hydrophobic group and a second monomer unit having a pendant hydrophilic group.

Another aspect of the disclosure provides a method of making a lipid nanodisc, the method comprising contacting a lipid and an acryloyl-based copolymer comprising a first monomer unit having a pendant hydrophobic group and a second monomer unit having a pendant hydrophilic group to form a lipid nanodisc comprising a lipid bilayer comprising a first hydrophilic face and a second hydrophilic face opposing the first hydrophilic face, and a hydrophobic edge between the opposing hydrophilic faces and the copolymer encircling the hydrophobic edge of the lipid bilayer.

Another aspect of the disclosure provides a method of characterizing a membrane protein, the method including contacting a lipid nanodisc of the disclosure with a membrane protein to form a membrane protein-nanodisc including the membrane protein spanning across the lipid bilayer from the first hydrophilic face to the second hydrophilic face, and characterizing the lipid nanodisc including the membrane protein.

Further aspects and advantages will be apparent to those of ordinary skill in the art from a review of the following detailed descriptions. While the compositions and methods are susceptible of embodiments in various forms, the description hereafter includes specific embodiments with the understanding that the disclosure is illustrative, and is not intended to limit the invention to the specific embodiments described herein.

DETAILED DESCRIPTION

Provided herein are copolymer-based lipid nanodiscs and methods of making and using same. In general, the copolymer-based lipid nanodiscs disclosed herein include an acryloyl-based copolymer comprising a monomer unit having a pendant hydrophilic group and a monomer unit having a pendant hydrophobic group.

The copolymers described herein provide one or more advantages, for example, extracting membrane proteins without the use of low-molecular weight detergents, forming nanodiscs with native lipid bilayers, solubilization of lipid bilayers, and forming nanodiscs over wide pH ranges and sizes. Additionally, the copolymer is advantageously stable for periods of at least 6 months, can be stored as a powder, and does not require purification by high performance liquid chromatography. Furthermore, the lipid nanodiscs of the disclosure provide the unique advantage of enabling the application of various biophysical techniques typically employed in the structural study of membrane proteins, such as circular dichroism, UV/vis, and fluorescence spectroscopy, which may be otherwise unsuitable for lipid nanodiscs previously reported in the art.

Copolymer

The copolymer of the disclosure is an acryloyl-based copolymer comprising a first monomer unit having a pendant hydrophobic group and a second monomer unit having a pendant hydrophilic group. As used here, the term "acryloyl-based" means the copolymer of the disclosure is formed, in part or in whole, from monomers including or derived from an acryloyl group (e.g., a carbonyl group (C=O) bonded to an adjacent alkenyl group (C=C) such as a vinyl group). As used herein, and unless specified otherwise, "acryloyl-based" encompasses monomers including or derived from acrylate, alkacrylate (e.g., methacrylate), acrylamide, and/or alkacrylamide (e.g., methacrylamide). For example, at least 75 mol %, at least 80 mol %, at least 90 mol %, at least 95 mol %, at least 97 mol %, or at least 99 mol % of the monomer units of an acryloyl-based copolymer are derived from acryloyl monomers as alkenyl or vinyl polymerization reaction products thereof.

Figure 1:
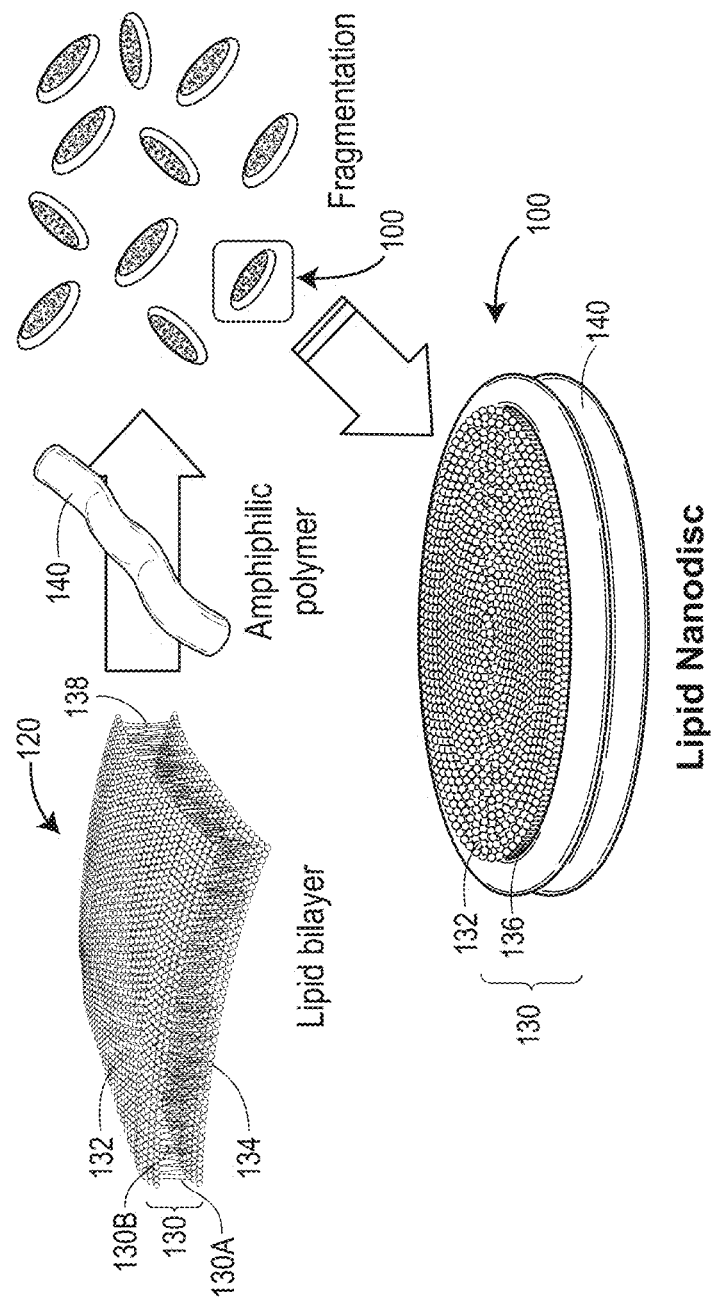
FIG. 1 shows a simplified schematic representation of lipid nanodisc formation.

The copolymer of the disclosure can include a first monomer unit having a pendant hydrophobic group and a second monomer unit having a pendant hydrophilic group. Without intending to be bound by theory, it is believed that the hydrophobic pendant groups and hydrophilic pendant groups of the copolymer interact with the hydrophobic acyl chains and anionic phosphate headgroup of lipids, respectively, to enable the formation of a lipid nanodisc formation surrounded by the copolymer. A simplified schematic representation of the formation of lipid nanodiscs is shown in FIG. 1.

In some embodiments, the copolymer can be a random copolymer. The inventors have surprisingly and advantageously found that the copolymers of the disclosure, regardless of the arrangement of hydrophilic and hydrophobic monomers in the copolymer structure, mimic the structure of natural amphipathic α-helical peptides that have been found to form nanodiscs. By the use of hydrophilic and hydrophobic pendant groups, the inventors have found a copolymer that provides an amphipathic structure upon interaction with a lipid bilayer.

In embodiments, at least one of the first monomer unit and the second monomer unit is derived from an acrylate, an acrylamide, a $C_{1-6}$ alkylacrylate (e.g., $C_1$, $C_2$, or $C_3$ alkylacrylate), or a $C_{1-6}$ alkylacrylamide (e.g., $C_1$, $C_2$, or $C_3$ alkylacrylamide).

The copolymer of the disclosure can comprise a first monomer unit and a second monomer unit, wherein the first monomer unit and the second monomer unit are independently selected from the group consisting of a polymerization reaction product of an acrylate according to Formula 1 and a polymerization reaction product of an acrylamide according to Formula 2:

$$R_1R_2C=CR_3-C(=O)-O-R_4 \qquad (1)$$

$$R_1R_2C=CR_3-C(=O)-NR_4R_5 \qquad (2)$$

wherein $R_1$, $R_2$, $R_3$, and $R_5$ are independently selected from H and $C_{1-6}$ alkyl (e.g., $C_1$, $C_2$, or $C_3$ alkyl), and $R_4$ is the pendant hydrophobic group for the first monomer unit or the pendant hydrophilic group for the second monomer unit.

In addition to, or in the alternative of, the first monomer unit and second monomer unit being selected from the group consisting of a polymerization reaction product of an acrylate according to Formula 1 and a polymerization reaction product of an acrylamide according to Formula 2, the copolymer can comprise monomer units that are not acryloyl-based. In embodiments wherein non-acryloyl-based monomer units are included, the molecular weight is less readily controlled during the polymerization process. In some embodiments, the polymer can be derived from the polymerization of more than two monomer species. That is, the polymer can be derived from three (terpolymer), four (quaterpolymer), five, six, seven, or more different monomer species, whether acryloyl-based monomers, non-acryloyl-based monomers, or combinations thereof.

As used herein, "non-acryloyl-based" monomer units include any monomer unit that does not include or is not derived from an acryloyl group. Suitable non-acryloyl-based monomer units are known in the art and can be derived from monomers including, but not limited to, vinyl alkanes (e.g., ethylene, propylene, butylene), vinyl acetates, vinyl ethers, vinyl alcohols (e.g., 1-hexen-6-ol) or combinations of the foregoing. Examples of non-acryloyl-based monomer units include, but are not limited to, substituted or unsubstituted 1-hexen-6-ol, 1-hexene, propylene, α-butylene (1-butene), 1-pentene, 3-methyl-1-butene (isopentene), 4-methyl-1-pentene, 3-methyl-1-pentene, 2-methyl-1-pentene, 3,3-dimethyl-1-butene, and 2,3-dimethyl-1-butene.

The hydrophobic pendant group is not particularly limited. Suitable hydrophobic pendant groups include, but are not limited to, $C_{4-14}$ hydrocarbons (e.g., at least $C_4$, $C_5$, or $C_6$ hydrocarbons and/or up to $C_5$, $C_{10}$, $C_{12}$, or $C_{14}$ hydrocarbons). As used herein, the term "hydrocarbon" refers to any straight-chained, branched, or cyclic group including or consisting of carbon and hydrogen, wherein the group can be saturated or unsaturated. In some embodiments, the hydrocarbon can be a fluorinated hydrocarbon, wherein one or more of the hydrogen atoms of the hydrocarbon has been replaced with a fluorine atom. Examples of suitable fluorinated hydrocarbons, include but are not limited to, perfluorooctane, perfluorohexane, hexafluoroethane, and perfluoromethylcyclohexane. The term $C_n$ means the hydrocarbon has "n" carbon atoms. For example, $C_4$ hydrocarbon refers to a hydrocarbon that has four carbon atoms. $C_{1-7}$ refers to a hydrocarbon having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of hydrocarbon groups include methyl, ethyl, n-propyl, isopropyl, n-butyl, sec-butyl (2-methylpropyl), t-butyl (1,1-dimethylethyl), 3,3-dimethylpentyl, 2-ethylhexyl, n-octyl, n-nonyl, and n-decyl. Unless otherwise indicated, a hydrocarbon group can be an unsubstituted hydrocarbon group or a substituted hydrocarbon group.

The hydrophobic pendant group can comprise a linear $C_{4-14}$ hydrocarbon, a branched $C_{4-14}$ hydrocarbon, a cyclic $C_{4-14}$ hydrocarbon, or combinations thereof. In some embodiments, the linear $C_{4-14}$ hydrocarbon, the branched $C_{4-14}$ hydrocarbon, or the cyclic $C_{4-14}$ hydrocarbon is a fluorinated hydrocarbon. In some embodiments, the hydrocarbon is a saturated hydrocarbon. In other embodiments, the hydrocarbon is an unsaturated hydrocarbon. Without intending to be bound by theory, hydrophobic pendant groups having unsaturated hydrocarbons can result in decreased polymerization rates and, therefore, decreased copolymer yield, as the unsaturated groups can interfere with the free-radical polymerization reaction. However, copolymers comprising unsaturated hydrophobic pendant groups can still effectively form the lipid nanodiscs of the disclosure.

In embodiments where the hydrocarbon is unsaturated, the unsaturation suitably is not conjugated. Without intending to be bound by theory, it is believed that conjugation in the pendant hydrophobic and/or hydrophilic group can cause interference in the absorption properties of the membrane proteins that can be associated with the lipid nanodiscs of the disclosure. Such interference can inhibit the use of commonly used biophysical techniques such as fluorescence, UV/vis and circular dichroism. Accordingly, in embodiments, the copolymers of the disclosure are free of styrene. In embodiments, the copolymers are free of all aromatic groups.

Examples of suitable $R_4$ groups for the first monomer unit as seen in Formulas (1) and (2) include, but are not limited to —$CH_3$, $CH_2CH_3$, $CH_2CH_2CH_3$, $CH_2CH_2CH_2CH_3$,

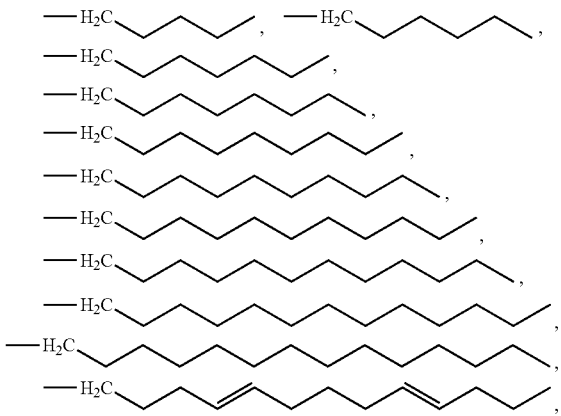

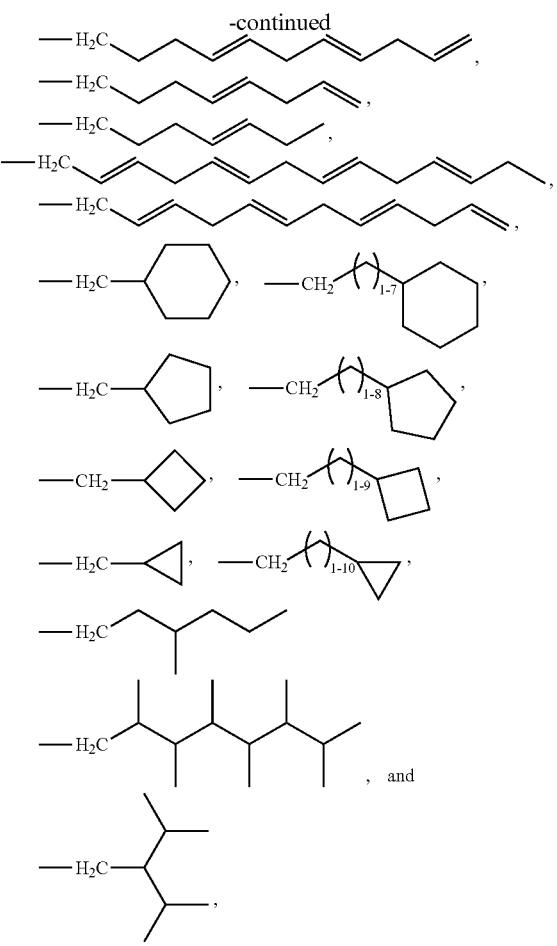

as well as partially or per-fluorinated analogs of the foregoing.

The second monomer unit having a pendant hydrophilic group is not particularly limited, that is, it can include any hydrophilic group suitable to solubilize the lipid nanodisc in an aqueous solution. In some embodiments, the pendant hydrophilic group include one or more of hydroxyl, amino, ether, carboxylic acid, carboxylate, phosphate, phosphonate, phosphocholine, carboxylic ether, carboxylic ester, phosphate ester, amide, phosphonamide, ammonium, or salts of the foregoing. The pendant hydrophilic group can be positively charged, negatively charged, zwitterionic, or neutral. Positively charged hydrophilic groups can include, but are not limited to, ammonium cations (e.g. alkylammonium cations, such as mono-, di-, tri-, or tetra-alkylammonium cations). Negatively charged hydrophilic groups can include, but are not limited to, carboxylate or phosphate.

The pendant hydrophilic group can be a chelating group or can further include a chelating group. The chelating group can further include a metal ion bound thereto. A pendant hydrophilic group including a fluorescent group or chelating group having a metal ion bound thereto can advantageously provide a spectroscopic tag to provide additional characterization of the lipid nanodiscs including the copolymers of the disclosure. Suitable fluorescent tags can include, but are not limited to, cyanine5 amine and Alexa fluor 488. Suitable metal chelating tags include, but are not limited to, ethylenediaminetetraacetic acid (EDTA) and lanthanide binding tags.

Examples of suitable $R_4$ groups for the second monomer unit, as seen in Formulas (1) and (2) include, but are not limited to:

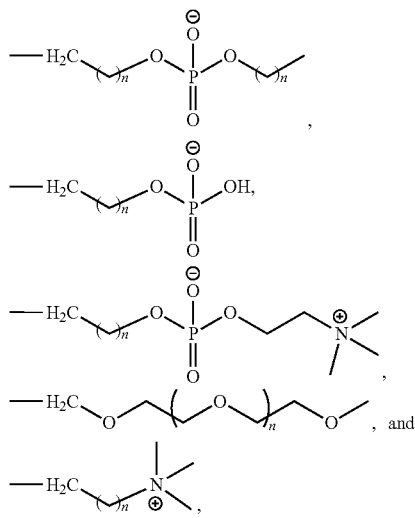

wherein n can be between 1 and 14, such as

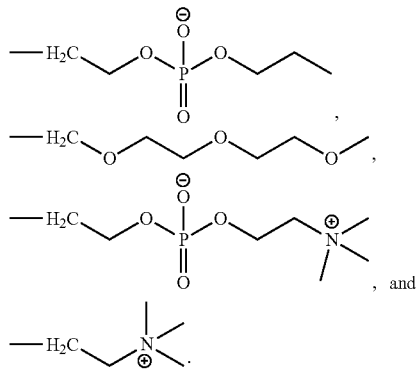

In some embodiments, the first monomer unit is derived from butyl methacrylate. In some embodiments, the second monomer unit is derived from a methacroylcholine salt. More specifically, the second monomer unit can be derived from methacroylcholine chloride. In some embodiments, the copolymer comprises a first monomer unit derived from butyl methacrylate and a second monomer unit derived from methacroylcholine chloride.

The acryloyl-based copolymer of the disclosure can comprise monomer units having a pendant hydrophobic group at a mole fraction of about 0.20 to about 0.90, based on the total number of monomer units having a pendant hydrophobic group and monomer units having a pendant hydrophilic group. As used herein, this mole fraction, f, can also be referred to as the "hydrophobicity" or "hydrophobic fraction." In embodiments, the hydrophobic fraction ranges from about 0.20 to about 0.90, about 0.24 to about 0.85, or about 0.40 to about 0.60, for example about 0.20, 0.24, 0.25, 0.26, 0.33, 0.39, 0.40, 0.43, 0.44, 0.50, 0.51, 0.55, 0.59, 0.60, 0.61, 0.62, 0.63, 0.65, 0.70, 0.71, 0.75, 0.80, 0.85, or 0.90. Without intending to be bound by theory, it is believed that as the hydrophobicity decreases, e.g., below about 0.2, the interaction of the copolymer, as a whole, with the hydrophobic regions of the lipid bilayer decreases, thereby decreasing or inhibiting the ability of the copolymer to solubilize the lipid bilayer and/or induce fragmentation of a lipid bilayer to form nanodiscs. Similarly, without intending to be bound by theory, as the hydrophobicity increases, e.g., above about 0.8, the interaction of the copolymer, as a whole, with the hydrophobic regions of the lipid bilayer increases, resulting in the formation of small particles likely to be spherical polymer micelles, rather than the desired lipid nanodiscs.

The molecular weight of the acryloyl-based copolymer of the disclosure is not particularly limited. The copolymer can have a number-average molecular weight ($M_n$) in a range from about 1.5 kg/mol to about 15 kg/mol, about 1.7 kg/mol to about 14 kg/mol, or about 3.0 kg/mol to about 9.0 kg/mol, for example, about 1.5, 1.7, 2.0, 2.9, 3.7, 3.9, 4.0, 4.2, 4.3, 4.7, 5.5, 6.1, 6.3, 6.7, 6.9, 7.1, 7.3, 7.4, 8.7, 9.0, 10.0, 11.0, 12.0, 13.0, 14.0, or 15.0 kg/mol. Without intending to be bound by theory, it is believed that as the number-average molecular weight of the copolymer decreases, the ability of the copolymer to disrupt a lipid vesicle and form a lipid nanodisc decreases because the size (width) of the polymer band that forms around the lipid nanodisc decreases. Further, it is believed that when the number-average molecular weight decreases beyond, e.g., 3 kg/mol or 1.5 kg/mol, the size of the resulting polymer band becomes too narrow to span the hydrophobic edge of the lipid bilayer, thereby inhibiting or preventing nanodisc formation. Accordingly, the number-average molecular weight of the polymer can be selected to promote nanodisc formation and stability. In general, a low molecular weight polymer in the foregoing ranges permits improved control over the size of the formed nanodiscs. If the molecular weight of the copolymer decreases beyond 1.0 kg/mol, however, the copolymer can behave as a detergent, leading to issues such as protein inactivation and sample aggregation. In addition, without intending to be bound by theory, it is believed that as the number-average molecular weight of the copolymer increases, the interaction of the copolymer with the lipid bilayer, as well as the inter- and intra-polymer interactions, increase, thereby providing a heterogeneous mixture of small particles and large fragments of lipid vesicles, rather than the desired lipid nanodiscs. Furthermore, if the molecular weight of the copolymer increase above, for example 15 kg/mol, the efficiency of nanodisc formation can decrease as a result of the increased viscosity of the copolymer solution.

The degree of polymerization (DP) of the copolymer is not particularly limited. The degree of polymerization of the acryloyl-based copolymer can range from about 10 to about 100, about 15 to about 95, about 30 to about 70, or about 40 to about 60, for example about 10, 12, 18, 20, 23, 24, 27, 28, 30, 35, 36, 37, 40, 41, 43, 48, 50, 55, 56, 60, 65, 70, 75, 78, 80, 82, 83, 90, 95 or 100.

Lipid Nanodiscs

The copolymer-based lipid nanodiscs disclosed herein further include a lipid. The lipid is not particularly limited. The lipid can include a natural cell membrane extract. Suitable lipids include, but are not limited to phosphatidylethanolamines, phosphatidylcholines, phosphatidylglycerols, phosphatidylserines, cholesterols, sphingomyelin, gangliosides, lipopolysaccharides, phophatidylinositols, and derivatives of the foregoing. In some embodiments, the lipid comprises at least one of phosphatidylethanolamines, phosphatidylcholines, phosphatidylglycerols, phosphatidylserines, cholesterols, sphingomyelin, gangliosides, lipopolysaccharides, and phophatidylinositols. In some embodiments, the lipid is a phospholipid. In some embodiments, the phospholipid includes a phosphatidylcholine.

FIG. 1 illustrates a lipid nanodisc 100 according to the disclosure, which includes a lipid 120 and a copolymer (e.g., an acryloyl-based copolymer) 140. The lipid 120 in the nanodisc 100 forms a lipid bilayer 130 including a first hydrophilic face 132 and a second hydrophilic face 134, wherein the first hydrophilic face 132 and the second hydrophilic face 134 are opposing, and a hydrophobic edge 136 between the opposing hydrophilic faces 132, 134. The hydrophobic edge 136 is made up of the hydrophobic tails 138 from both layers of the lipid bilayer 130. The center of the hydrophobic edge 136 is the point at which the hydrophobic tail 138 from one layer 130A of the bilayer 130 meets the hydrophobic tail 138 from the second layer 130B of the bilayer 130. The nanodisc 100 further includes a copolymer 140 of the disclosure encircling the hydrophobic edge 136 of the lipid bilayer 130.

The lipid nanodiscs of the disclosure can have a diameter in a range of about 6 nm to about 100 nm, for example, about 6 nm to about 100 nm, about 10 nm to about 90 nm, about 20 nm to about 90 nm, about 30 nm to about 80 nm, about 40 nm to about 80 nm, about 50 nm to about 70 nm, or about 55 nm to about 65 nm. In some embodiments, the nanodisc has a diameter less than or equal to 40 nm, for example, in a range of about 6 nm to 40 nm, about 10 nm to about 35 nm, about 20 nm to about 35 nm, or about 25 nm to about 30 nm. In some embodiments, the nanodisc has a diameter greater than 40 nm, for example, 41 nm to about 100 nm, about 45 nm to about 90 nm, about 50 nm to about 80 nm, about 50 nm to about 70 nm, or about 60 nm. Nanodiscs having a diameter greater than 40 nm can be referred to as "macrodiscs." The size of the nanodisc can be controlled by changing the lipid:copolymer weight ratio during preparation. In general, as the amount of copolymer increases relative to the amount of lipid, the size of the resulting nanodisc decreases. Similarly, as the amount of copolymer decreases relative to the amount of lipid, the size of the resulting nanodisc increases.

In some embodiments, the lipid nanodisc can be characterized in that when a magnetic field is applied, the nanodisc aligns with the magnetic field. Such a characteristic can be advantageous, for example, when characterizing the nanodisc (or a membrane protein provided therein) by NMR spectroscopy.

The lipid nanodisc can further include a membrane protein. The membrane protein can be any protein that interacts with or is part of a biological membrane, and can be permanently anchored or temporarily anchored to a lipid bilayer. Suitable membrane proteins include, but are not limited to U-$^{15}$N Cytb5, cytochromes such as cytochrome b5, cytochrome P450, cytochrome P450 reductase, cytochrome c, outer membrane proteins or integral outer membrane proteins, photosystem II, voltage-gated ion channels, beta barrel, and G-protein-coupled receptors (GPCRs). When a membrane protein is included in the lipid nanodisc, the membrane protein spans across at least one half of the lipid bilayer, from one hydrophilic face to the center of the hydrophobic edge. In some embodiments, the membrane protein spans across the entire lipid bilayer from the first hydrophilic face to the second hydrophilic face at least once. In some embodiments, the membrane protein spans across the entire lipid bilayer from the first hydrophilic face to the second hydrophilic face more than once.

Method of Preparing Lipid Nanodisc

Further provided herein are methods of making a lipid nanodisc 100, the method including contacting a lipid 120 and an acryloyl-based or other copolymer 140 comprising a copolymer formed by the polymerization of a monomer having a pendant hydrophilic group and a monomer having a pendant hydrophobic group (FIG. 1). The method of making a lipid nanodisc can also include contacting a lipid and an acryloyl-based copolymer comprising a first monomeric unit having a pendant hydrophobic group and a second monomeric unit having a pendant hydrophilic group. Advantageously, the nanodiscs of the disclosure are easy to prepare, inexpensive and stable for up to a month. Furthermore, the nanodiscs of the disclosure can advantageously be characterized by common biophysical techniques, such as circular dichroism (CD), UV/Vis and fluorescence spectroscopy.

The lipid and copolymer can be any lipid and copolymer described herein. The method of preparing the lipid nanodisc includes contacting the lipid and the copolymer. In some embodiments the lipid is provided as a multilamellar vesicle. Without intending to be bound by theory, it is believed that when the lipid is provided as a multilamellar vesicle, the copolymer chains get inserted into the lipid bilayer and break the multilamellar vesicle into nanodisc shaped lipoparticles. The lipid can include a natural cell membrane extract.

The lipid can further include a membrane protein such that the resulting lipid nanodisc includes a membrane protein spanning across at least one half of the lipid bilayer from one hydrophilic face to the center of the hydrophobic edge. In some embodiments, the lipid includes a membrane protein such that the resulting lipid nanodisc includes a membrane protein spanning across the entire lipid bilayer from one hydrophilic face to the second hydrophilic face at least once. In some embodiments, the membrane protein spans across the entire lipid bilayer from the first hydrophilic face to the second hydrophilic face more than once.

The contacting step can include admixing the lipid and the copolymer in solution. An aqueous solution of copolymer can be prepared prior to contacting the copolymer with the lipid. A lipid dispersion can be prepared prior to contacting the copolymer with the lipid. The contacting step can include admixing the copolymer solution and the lipid suspension. The solutions and suspensions of the disclosure can be substantially free of a detergent. As used herein, "substantially free" means that the solution and/or suspension does not contain significant amounts of a purposefully added detergent. Thus, incidental or background quantity of detergents (e.g., less than about 100 ppb) can be present in the solution and/or suspension and be within the scope of the disclosure.

The contacting step can optionally further include providing a buffer to regulate the pH of the solution. Without intending to be bound by theory it is believed that in some embodiments, the pH of the solution can affect the charge of the copolymer, thus ultimately affecting solubility of the copolymer and stability of the resulting nanodiscs. The contacting step can be carried out at any suitable pH in which the copolymer is stable and soluble, for example, in a range of about 0 to about 14, about 1 to about 12, about 2 to about 11, about 2.5 to about 10, or about 3 to about 9, for example, about 2.5, about 3, about 3.5, about 4, about 4.5, about 5, about 5.5, about 6, about 6.5, about 7, about 7.5, about 8, about 8.5, about 9, about 9.5, or about 10.

The weight ratio of the lipid to the copolymer of the disclosure provided in the methods of the disclosure is not particularly limiting. The lipid and the copolymer can be provided in a ratio of about 9:1 to about 1:9 by weight, for example, a weight ratio of about 8:1 to about 1:8, about 6:1 to about 1:6, about 4:1 to about 1:4, or about 1:1. In some embodiments, the lipid and the copolymer are provided in a ratio in a range of about 8:1 to about 1:3, by weight. In some embodiments, the lipid and the copolymer are provided in a ratio in a range of about 4:1 to about 1:1.5, or about 3:1 to about 1:1, by weight. In general, as the weight of the copolymer is increased relative to the weight of the lipid, the maximum diameter of the resulting nanodiscs decrease. In some embodiments, there is an asymptotic value for the relative amount of the copolymer above which there is no further substantial decrease in the size/diameter of the nanodisc.

The formation of the copolymer-based lipid nanodiscs of the disclosure can be confirmed and characterized using a number of well-known techniques such as static light scattering (SLS), dynamic light scattering (DLS), size-exclusion chromatography (SEC), Fourier-transform infrared spectroscopy (FT-IR), solid-state nuclear magnetic resonance (ssNMR), and transmission electron microscopy (TEM). Advantageously, when the nanodiscs are less than or equal to about 40 nm, the structure of the nanodiscs can be determined based on solution NMR techniques and when the nanodiscs are greater than about 40 nm, the nanodiscs can be magnetically-aligned which is advantageous for solid-state NMR studies. Furthermore, as the copolymers of the disclosure can be free of styrene and/or aromatic groups, the nanodiscs can be characterized using biophysical techniques such as circular dichroism (CD), ultraviolet-visible spectroscopy (UV/Vis), and fluorescence spectroscopy.

Method of Characterizing Membrane Proteins

The disclosure further provides a method of characterizing a membrane protein, the method including contacting a lipid nanodisc of the disclosure with a membrane protein to form a membrane protein-nanodisc including the membrane protein spanning across the lipid bilayer from the first hydrophilic face, to the second hydrophilic face of the lipid nanodisc and characterizing the lipid nanodisc including the membrane protein. In some embodiments, the membrane protein spans across the entire lipid bilayer from the first hydrophilic face to the second hydrophilic face more than once. The membrane protein can be any membrane protein disclosed herein. In some embodiments, the membrane protein spans across half of the lipid bilayer from one hydrophilic face to the center of the hydrophobic edge.

In some embodiments, the contact includes admixing the lipid nanodisc and membrane protein in solution. In some embodiments, the solution is substantially free of detergent.

Characterization can include at least one of a structural characterization of the membrane protein or a functional characterization of the membrane protein. Suitable membrane protein characterization methods include solution and solid state nuclear magnetic resonance (NMR), circular dichroism (CD), electron paramagnetic resonance (EPR), Fourier transform infrared spectroscopy (FTIR), resonance Raman spectroscopy, ultraviolet-visible spectroscopy (UV/vis), cryo-electron microscopy (cryo-EM), surface plasmon Raman spectroscopy, sum frequency generation (SFG), fluorescence, including single molecule fluorescence and coherent anti-Stokes Raman (CARS), small angle x-ray scattering (SAXS), scanning electron microscopy (SEM), atomic force microscopy (AFM) and enzymatic assays Membrane protein structure and dynamics can be characterized using NMR techniques. For example, membrane protein-nanodiscs having a diameter of about 40 nm or less can be characterized using solution NMR and membrane protein-nanodiscs having a diameter greater than about 40 nm can be characterized using solid state NMR. Advantageously, the nanodiscs of the disclosure can include additional features for enhancing characterization by NMR, for example, the nanodisc can be characterized in that when a magnetic field is applied, the nanodisc aligns with the magnetic field and the nanodisc optionally includes a chelating group having a metal ion bound thereto as part of the pendant hydrophilic group which allows paramagnetic resonance characterization.

Magnetically aligned nanodiscs provide a novel membrane mimetic environment for the structural investigation of several membrane proteins by measuring $^1$H-$^{15}$N heteronuclear dipolar couplings. One of the most popular approaches to measure heteronuclear dipolar couplings in ssNMR is the 2D separation of heteronuclear dipolar interactions according to chemical shifts. This class of experiments is known as Separated Local Field (SLF) spectroscopy. Polarization Inversion and Spin Exchange at Magic Angle (PISEMA) is a well-known and useful NMR technique for structural studies of a variety of biological systems.

The copolymer-based lipid nanodiscs of the disclosure can be advantageous for one or more applications including, reconstitution of membrane proteins, purification of membrane proteins or peptides, drug delivery, and controlling the aggregation of amyloid peptides or proteins.

The above described aspects and embodiments can be better understood in light of the following examples, which are merely intended to be illustrative and are not meant to limit the scope in any way.

EXAMPLES

Example 1: Preparation of Copolymer

A polymethacrylate copolymer was prepared via free radical polymerization initiated by azobisisobutyronitrile (AIBN) according to the following reaction scheme:

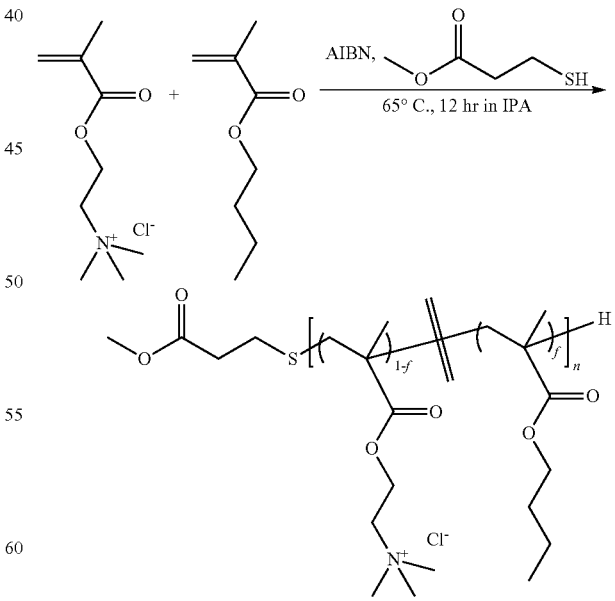

In particular, 0.2 mmol of methacroylcholine chloride supplied by TCI Co., Ltd. (Tokyo, Japan), 100 µL of AIBN in isopropyl alcohol (8.21 mg/mL, 5 µmol, 1 mol % total monomers), and 100 µL of 3-mercaptopropionate (MMP) in isopropyl alcohol (30.04 mg/mL, 25 μmol, 5 mol % total monomers) were dissolved in 3004 isopropyl alcohol. The solution was bubbled with nitrogen gas for 5 minutes to remove any dissolved oxygen. To the solution, 0.3 mmol of butyl methacrylate supplied by TCI Co., Ltd. (Tokyo, Japan) was added. The solution was stirred at 65° C. overnight, after which the isopropyl alcohol solvent was removed in vacuo and the copolymer was dissolved in approximately 3004 of methanol. The resultant copolymer solution was added to ice cold diethyl ether to induce precipitation of the copolymer. The resultant precipitate was collected via centrifugation and lyophilized from aqueous solutions to give a copolymer in the form of a white powder. The copolymer was stored at room temperature until use.

Figure 2:
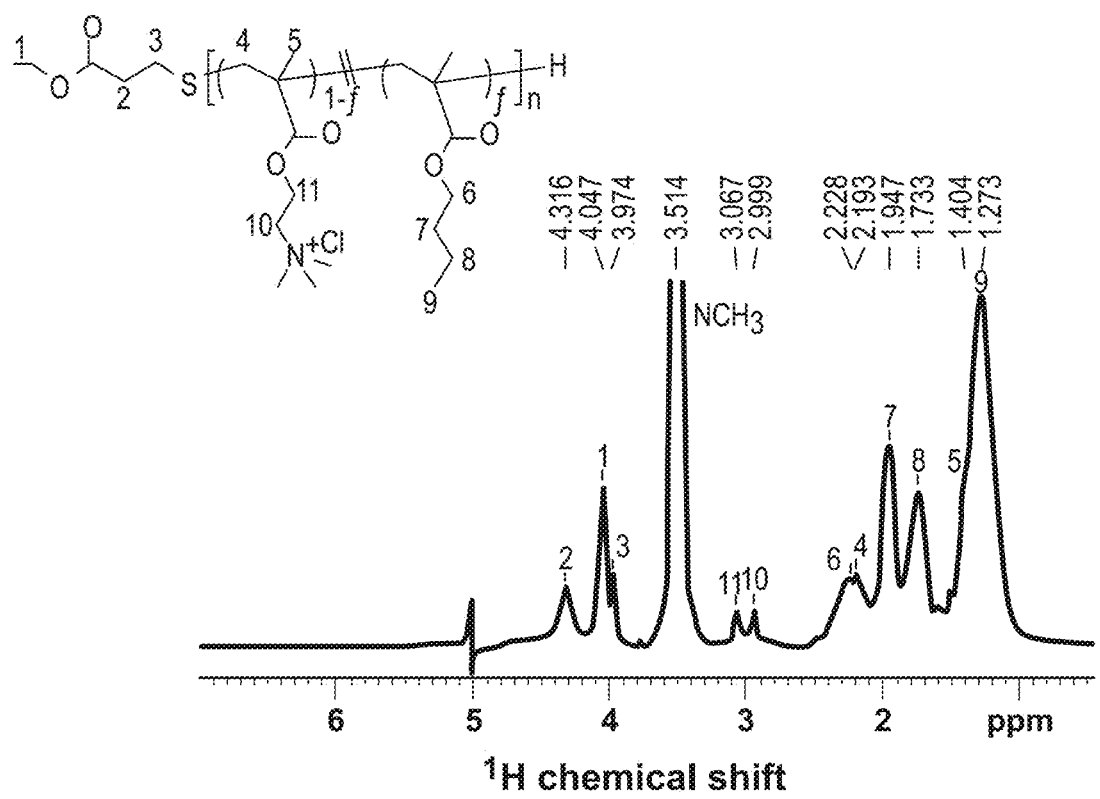
FIG. 2 shows a sample $^1$H NMR spectrum of a copolymer according to the disclosure.

The resultant copolymer was characterized via $^1$H NMR analysis to determine the degree of polymerization (DP), the number-average molecular weight ($M_n$), and the mole fraction of butyl methacrylate, f, of the copolymer. The spectrum was obtained at 25° C. by dissolving 2 mg of the copolymer sample in 6004 of 100% $D_2O$ to provide a final concentration of 0.8 mM. The integration of signals from the following chemical groups was used for the characterization of the copolymer: methoxy terminal of the polymethacrylate backbone ($CH_3OCO$, 4.0 ppm, 3H), methylene group in choline side chains (($CH_3)_3N+CH_2$, 2.9 ppm, 2H), and the methylene in both monomer units ($COOCH_2$, 2.2 ppm, 2H). A representative spectrum for a copolymer according to the disclosure having a hydrophobicity of 0.60 and a number-average molecular weight of 4.7 kg/mol is demonstrated in FIG. 2.

Additional copolymers having various hydrophobicity fractions and molecular weights were prepared by varying the amount of MMP and the feed ratios of the methacroylcholine chloride and butyl methacrylate monomers.

Thus, Example 1 demonstrates the preparation of an acryloyl-based copolymer according to the disclosure.

Example 2: Preparation and Analysis of Copolymer-Based Lipid Nanodiscs

Large unilamellar vesicles (LUVs) having a diameter of 100 nm were prepared by dissolving 10 mg of 1,2-dimyristoyl-sn-glycero-3-phosphocholine (DMPC) from Avanti Polar Lipids, Inc. (Alabaster, AL, USA) in 1 mL of chloroform. The solvent was evaporated under a stream of nitrogen gas and the residual trace solvent was completely removed in vacuo for three hours to provide a thin lipid film on the wall of a glass vial. The resultant lipid film was then hydrated by vertex mixing with 10 mM HEPES buffer (pH=7.4, 150 mM NaCl) at 40° C. To homogenize the size of LUVs, the liposome dispersion was subjected to five freeze-and-thaw cycles at −196° C. and 50° C., followed by extrusion (11 times) through stacked 100 nm polycarbonate membrane filters installed in the LIPOSOFAST miniextruder from Avestin.

Figure 3A:
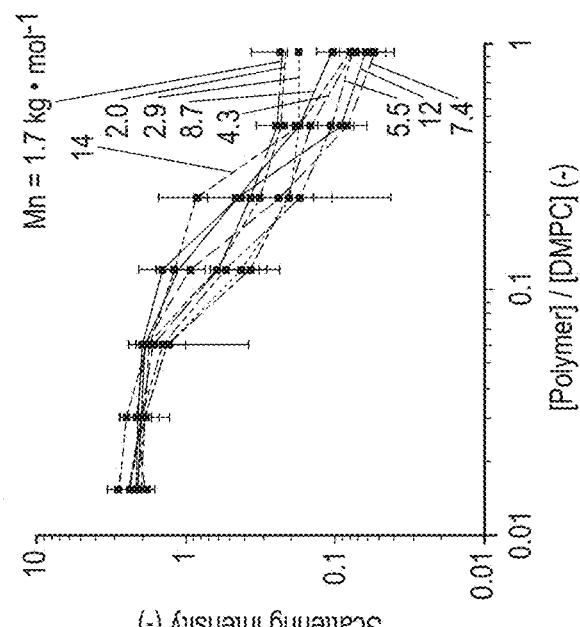
FIG. 3A shows the visual change in turbidity as a result of copolymer-induced fragmentation of a DMPC lipid membrane.

The solubilization of the vesicles in solutions of the copolymers of Example 1 was determined by adding 2 μL of a dimethyl sulfoxide (DMSO) stock solution of the copolymer to 198 μL of the hydrated vesicle solution and mixing using a mechanical pipette. The final concentration of the phospholipids in the copolymer-vesicle mixture was set to 100 μM and incubated for 30 minutes at room temperature prior to measurement. The addition of the copolymers from Example 1 to the DMPC vesicles resulted in a decrease of the solution turbidity, reflecting the copolymer-induced fragmentation of vesicles and resulting lipid nanodisc formation, as shown in FIG. 3A.

To further examine the effects of copolymer concentration, hydrophobicity, and molecular weight of the copolymer on vesicle fragmentation, the scattering intensity or turbidity was monitored by varying the copolymer:lipid ratio. Light scattering and hydrodynamic diameter of nanodiscs were measured using a dynamic light scattering spectrometer equipped with a laser diode illuminating at 665 nm (ELS-Z1000ZS, Otsuka Electronics Co., Ltd., Osaka, Japan). Size distribution of nanodiscs in an aqueous solution was obtained by analyzing a time course of scattered light intensity at an angle of 165° from the incident light with the Contin method. The sample temperature was maintained at 25° C. by the thermostat temperature controller installed in the equipment. The sample dispersion was filtrated using commercially available hydrophilic syringe filter with 450 nm pores to remove any dust from the sample prior to measurement.

Figure 3B:
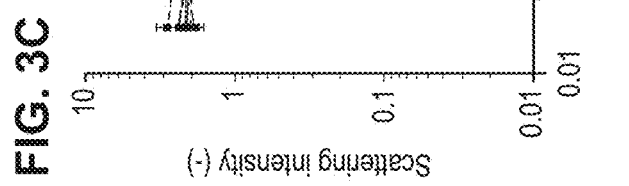
FIG. 3B shows the effect of the hydrophobicity of a copolymer on the copolymer-induced fragmentation of a DMPC lipid membrane.
Figure 3C:
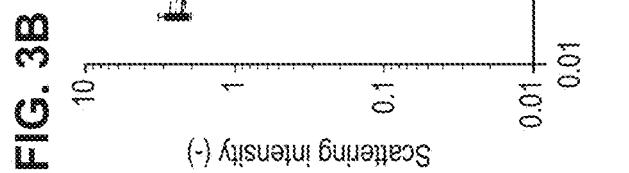
FIG. 3C shows the effect of the molecular weight of a copolymer on the copolymer-induced fragmentation of a DMPC lipid membrane.

As shown in FIG. 3B, some polymers with moderate hydrophobicity fraction (f) of around 0.3 to 0.6 induced a significant decrease in the scattering light intensity with increasing copolymer concentration, reflecting the fragmentation of the vesicular membrane. In contrast, polymers having extreme hydrophobicity fractions, such as 0.85 or 0.24, were found to be ineffective in the solubilization of the vesicles. Further shown in FIG. 3C, a copolymer with a relatively low molecular weight of around 3 kg/mol was ineffective in vesicle solubilization when compared to a large molecular weight copolymer, reflecting that a short copolymer cannot cover the hydrophobic thickness of the lipid bilayer.

Example 3: Morphology of Copolymer-Based Lipid Nanodisc

The morphology of the copolymer-lipid complex was examined by negative-stain transmission electron microscopy (TEM). Lipid nanodiscs formed from mixing the LUVs with polymers having differing hydrophobic fractions and molecular weights were analyzed by TEM to determine the polymers' effectiveness in inducing vesicle fragmentation and nanodisc formation.

Figure 4A:
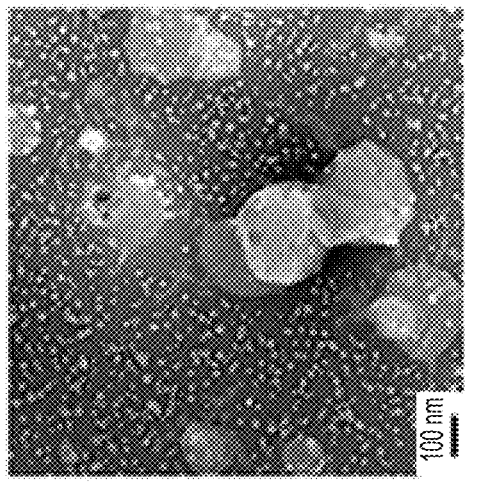
FIG. 4A shows the change in morphology of the copolymer-lipid complex via negative-stain TEM images of a copolymer-lipid complex when the copolymer has a hydrophobicity of 0.60 and a molecular weight of 4.7 kg/mol.
Figure 4B:
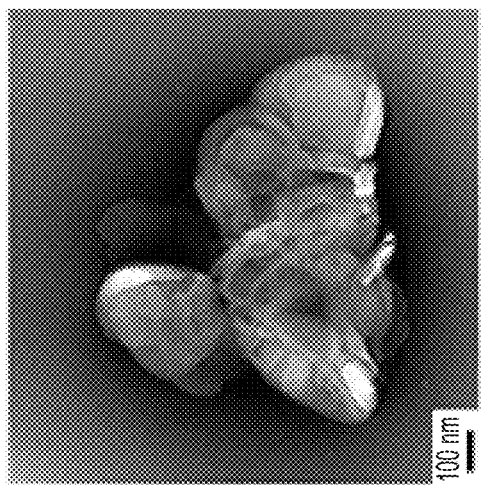
FIG. 4B shows the change in morphology of the copolymer-lipid complex via negative-stain TEM images of a copolymer-lipid complex when the copolymer has a hydrophobicity of 0.24 and a molecular weight of 6.1 kg/mol.
Figure 4C:
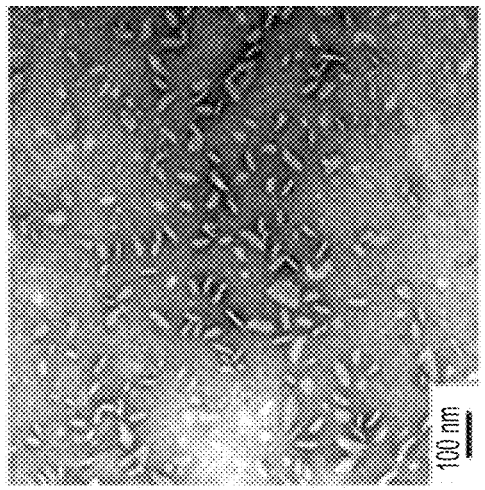
FIG. 4C shows the change in morphology of the copolymer-lipid complex via negative-stain TEM images of a copolymer-lipid complex when the copolymer has a hydrophobicity of 0.85 and a molecular weight of 6.1 kg/mol.

As shown in FIG. 4A, a copolymer having a hydrophobicity of 0.60 and a molecular weight of 4.7 kg/mol resulted in a homogeneous oval-shaped assembly of nanodiscs, reflecting the lipid bilayer nanodisc formation. Nanodiscs formed from polymers having very low hydrophobicity values (e.g., 0.24) and very high hydrophobicity values (e.g., 0.85), however, did not show effective or homogeneous fragmentation of the vesicles, as shown in FIG. 4B and FIG. 4C, respectively.

Figure 4D:
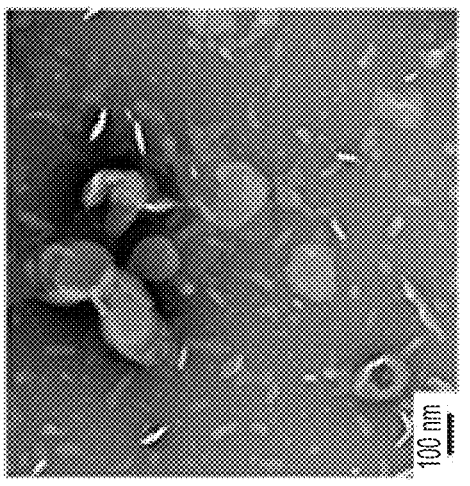
FIG. 4D shows the change in morphology of the copolymer-lipid complex via negative-stain TEM images of a copolymer-lipid complex when the copolymer has a hydrophobicity of 0.61 and a molecular weight of 1.7 kg/mol.
Figure 4E:
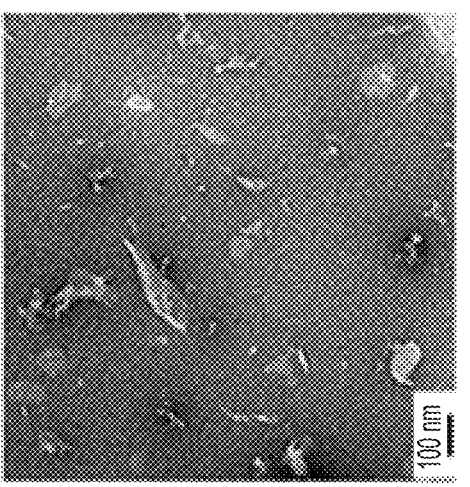
FIG. 4E shows the change in morphology of the copolymer-lipid complex via negative-stain TEM images of a copolymer-lipid complex when the copolymer has a hydrophobicity of 0.63 and a molecular weight of 14 kg/mol.

Additionally, a copolymer with a low molecular weight (e.g., 1.7 kg/mol) was found to partially disrupt lipid vesicles, as confirmed from the formation of a vesicle/nanodisc mixture, as shown in FIG. 4D. In contrast, a large molecular weight copolymer (e.g., 14 kg/mol) was found to form a heterogeneous mixture of small particles and large fragments of DMPC lipid vesicles, as shown in FIG. 4E.

Figure 4F:
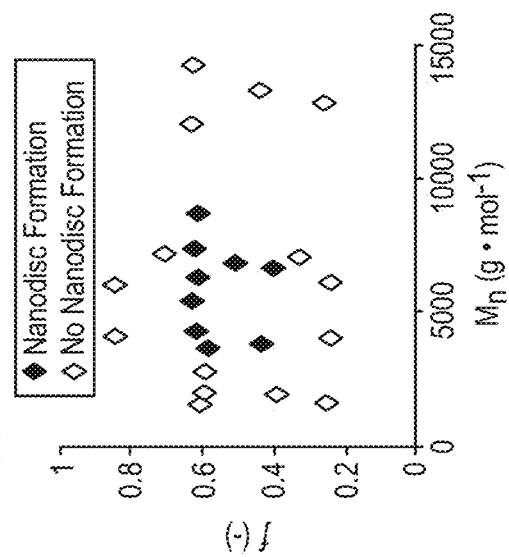
FIG. 4F shows the effect of the hydrophobicity and number average molecular weight of the copolymers on the formation of lipid nanodiscs.

The effects of the hydrophobic fraction (t) and molecular weight ($M_r$) of the copolymer on the lipid nanodisc formation, based on the solubilization assay as well as TEM observation are summarized in FIG. 4F. The solid-filled diamonds represent the ability of the polymers to form nanodiscs according to the disclosure.

The size, shape, and homogeneity of the lipid nanodiscs formed using the copolymers of the disclosure were further examined using cryo-TEM experiments. The cryo-TEM experiments confirmed that a 1:8 mixture of a copolymer having a hydrophobic fraction of 0.60 and a molecular weight of 4.7 kg/mol with the DMPC vesicles formed homogeneous nanodiscs, having a diameter of about 17 nm and a thickness of about 5.5 nm, which corresponded to the thickness of a single DMPC lipid bilayer.

Example 4: Fragmentation of Intact E. Coli Cells by Copolymer

The fragmentation of intact and live *Escherichia coli* cells using the polymers of the disclosure was analyzed using light scattering and TEM.

Figure 5A:
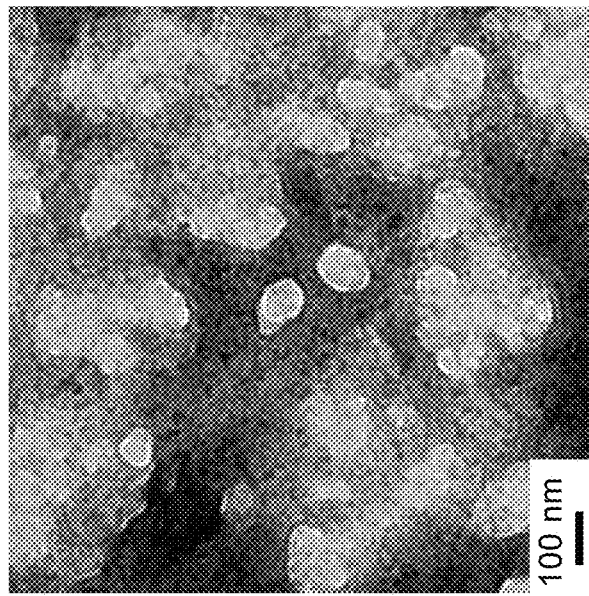
FIG. 5A shows the effect of a copolymer according to the disclosure on the scattering intensity of an *Escherichia coli* suspension.
Figure 5B:
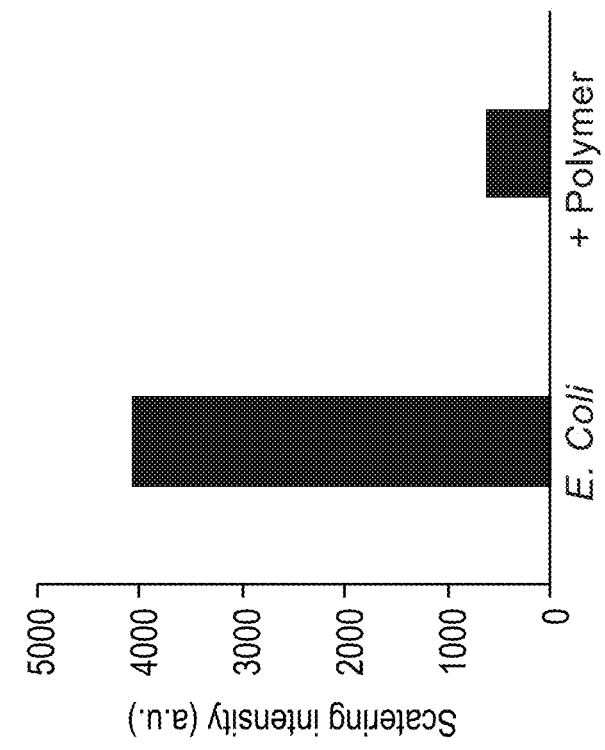
FIG. 5B shows a negative-stain TEM image of the copolymer-*E. coli* mixture.

The addition of a copolymer having a hydrophobic fraction of 0.60 and a molecular weight of 4.7 kg/mol dramatically decreased the light scattering intensity of the *E. coli* suspension. As shown in FIG. 5A and FIG. 5B, the addition of the copolymer of the *E. coli* suspension resulted in the formation of small particles, demonstrating the copolymer-induced disruption of the cells.

Thus, Example 4 demonstrates that the acryloyl-based nanodisc-forming copolymer of the disclosure is applicable not only to solubilized lipid vesicles, but also to intact cell membranes.

Example 5: Analysis of Amyloid Aggregation Using Nanodiscs

Thioflavin T (ThT)-based fluorescence and CD studies were performed to demonstrate the ability to measure the interactions of naturally-occurring C-amidated form of human islet amyloid polypeptide (hIAPP, also known as human amylin) and the lipid nanodiscs. Human amylin has been shown to play important role in insulin-producing islet death in type-2 diabetes.

A 9:1 molar ratio of DMPC:DMPG was dissolved in chloroform, dried under nitrogen gas, and the residual solvent was removed under high vacuum overnight. The resulting lipid film was rehydrated in 30 mM acetic acid buffer (pH 5.3) to make a 10 mg/ml stock solution of the lipid. A 450 μl aliquot of a 10 mg/ml in water solution of the copolymer was added to 300 μl lipid solution and incubated overnight. Excess copolymer was removed by washing with buffer using Amicon filter using a 30 kDa cutoff membrane. The resulting solution was used for experimental measurements reported in this study. All samples were prepared freshly before the start of each experiment.

Figure 6A:
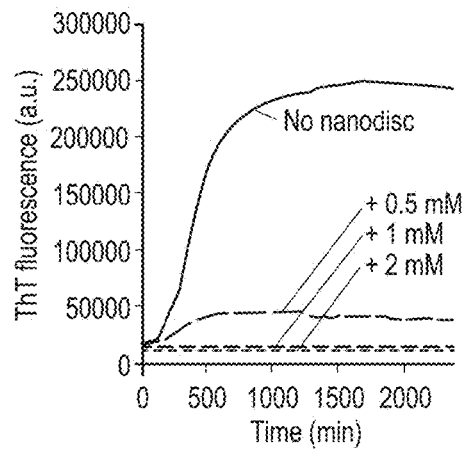
FIG. 6A shows fluorescence spectra for polymer nanodisc inhibition of human-IAPP (hIAPP) aggregation at a hIAPP concentration of 20 μM.
Figure 6C:
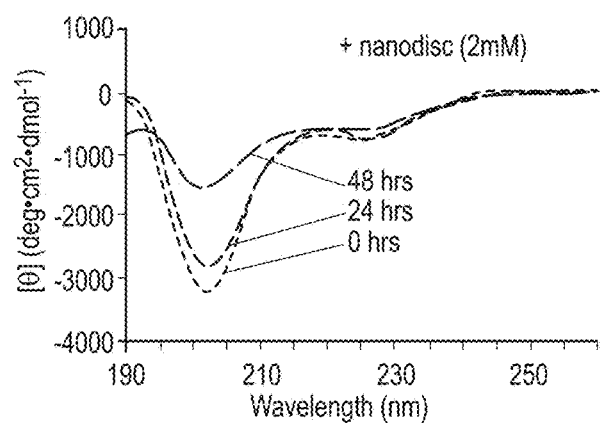
FIG. 6C shows CD spectra for polymer nanodisc inhibition of hIAPP aggregation at 20 μM hIAPP when in the presence of polymer nanodiscs according to the disclosure.
Figure 6B:
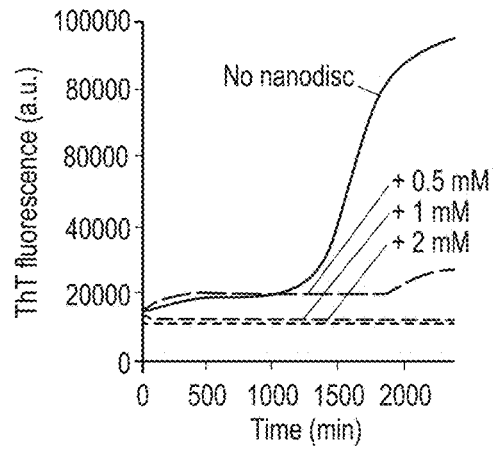
FIG. 6B shows fluorescence spectra for polymer nanodisc inhibition of human-IAPP (hIAPP) aggregation at a hIAPP concentration of 10 μM.

The ThT fluorescence results obtained in the absence of nanodiscs and in the presence of 9:1 DMPC:DMPG copolymer nanodiscs for two different concentrations (10 and 20 μM) of hIAPP are shown in FIG. 6A and FIG. 6B, respectively. In the absence of nanodiscs, the sigmoidal ThT traces suggest the time- and concentration-dependent aggregation of hIAPP to form amyloid fibers. In contrast, the addition of the nanodiscs significantly reduced and completely suppressed the ThT signal intensity. Accordingly, these results suggest the nanodiscs effectively suppressed the amyloid fiber formation of hIAPP.

Figure 6D:
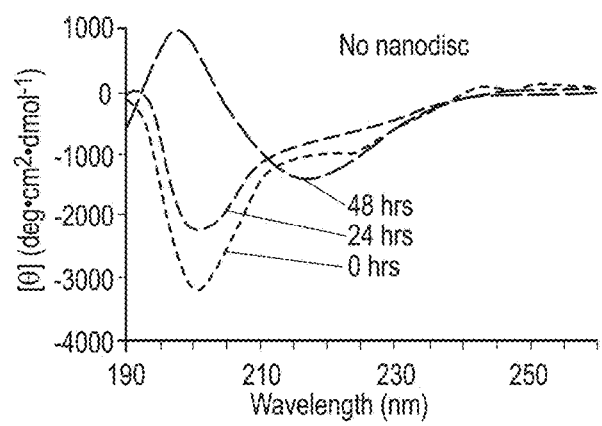
FIG. 6D shows CD spectra for polymer nanodisc inhibition of hIAPP aggregation at 20 μM hIAPP when in absence of polymer nanodiscs according to the disclosure.

Circular dichroism studies were performed to further confirm the suppression of fiber formation by the nanodiscs. As shown in FIG. 6C, the hIAPP peptide forms a helical structure in the presence of nanodiscs, indicated by the negative minima at 209 and 220 nm in the CD spectrum. In contrast, as would be expected, in the absence of nanodiscs, the hIAPP peptide forms a beta-sheet structure, as shown in FIG. 6D, indicated by the positive band at about 195 nm and the negative band at about 218 nm. It was also confirmed that the copolymer alone did not provide the stabilization of the helical structure seen with the lipid nanodisc of the disclosure.

Thus, Example 5 demonstrates the ability of the lipid nanodiscs of the disclosure to stabilize a helical intermediate of hIAPP. This unique application of the lipid nanodiscs is observable due to the lack of styrene and/or an aromatic group that can interfere with commonly used biophysical experiments such as CD and fluorescence.

What is claimed:

1. A lipid nanodisc, comprising: a disc shaped lipoparticle, wherein the disc shaped lipoparticle, comprises:
    a lipid bilayer comprising a first hydrophilic face and a second hydrophilic face opposing the first hydrophilic face, and a hydrophobic edge between the opposing hydrophilic faces; and
    an acryloyl-based copolymer encircling the hydrophobic edge of the lipid bilayer, wherein the acryloyl-based copolymer comprises a first monomer unit having an acryloyl group and a pendant hydrophobic group and a second monomer unit having an acryloyl group and a pendant hydrophilic group,
    wherein the acryloyl-based copolymer is free of aromatic groups.

2. The lipid nanodisc of claim 1, wherein the first monomer unit and the second monomer unit are independently selected from the group consisting of a polymerization reaction product of an acrylate according to Formula 1 and a polymerization reaction product of an acrylamide according to Formula 2:

wherein:
    R1, R2, R3, and R5 are independently selected from H and C1-6 alkyl; and
    R4 is the pendant hydrophobic group for the first monomer unit or the pendant hydrophilic group for the second monomer unit.

3. The lipid nanodisc of claim 1, wherein at least one of the first monomer unit and the second monomer unit is derived from an acrylate, an acrylamide, a C1-6 alkylacrylate, or a C1-6 alkylacrylamide.

4. The lipid nanodisc of claim 1, wherein the pendant hydrophobic group comprises a linear C4-14 alkyl group, a branched C4-14 alkyl group, a cyclic C4-14 alkyl group, or combinations thereof.

5. The lipid nanodisc of claim 1, wherein the first monomer unit is derived from butyl methacrylate.

6. The lipid nanodisc of claim 1, wherein the pendant hydrophilic group comprises one or more of hydroxyl, amino, ether, carboxylic acid, carboxylate, phosphate, phosphonate, phosphocholine, carboxylic ether, carboxylic ester, phosphate ester, amide, phosphonamide, ammonium, or salts of the foregoing.

7. The lipid nanodisc of claim 1, wherein the second monomer unit is derived from a methacroylcholine salt.

8. The lipid nanodisc of claim 1, wherein the acryloyl-based copolymer comprises monomer units having a pendant hydrophobic group at a mole fraction of about 0.20 to about 0.90, based on the total amount of monomer units having a pendant hydrophobic group and monomer units having a pendant hydrophilic group.

9. The lipid nanodisc of claim 1, wherein the acryloyl-based copolymer has a number-average molecular weight (Mn) from about 1.5 kg/mol to about 15 kg/mol.

10. The lipid nanodisc of claim 1, wherein the lipid comprises at least one of phosphatidylethanolamines, phosphatidylcholines, phosphatidylglycerols, phosphatidylserines, cholesterols, sphingomyelin, gangliosides, phosphatidylinositols, lipopolysaccharides, and derivatives of the foregoing.

11. The lipid nanodisc of claim 1, wherein the lipid comprises a natural cell membrane extract.

12. The lipid nanodisc of claim 1, wherein the lipid bilayer comprises a phosphatidylcholine, the first monomer unit is derived from butyl methacrylate, the second monomer unit is derived from methacroylcholine chloride, the acryloyl-based copolymer comprises monomer unit having a pendant hydrophobic group at a mole fraction of about 0.40 to about 0.60 based on the total amount of monomer units having a pendant hydrophobic group, and the acryloyl-based copolymer has a number-average molecular weight from about 3.0 kg/mol to about 9.0 kg/mol.

13. The lipid nanodisc of claim 1, wherein the nanodisc has a diameter in a range of about 6 nm to about 100 nm.

14. The lipid nanodisc of claim 1, wherein the nanodisc has a diameter less than or equal to 40 nm.

15. The lipid nanodisc of claim 1, wherein the nanodisc has a diameter greater than 40 nm.

16. The lipid nanodisc of claim 1, further comprising a membrane protein spanning across the lipid bilayer from the first hydrophilic face to the second hydrophilic face.

17. The lipid nanodisc of claim 1, characterized in that when a magnetic field is applied, the nanodisc aligns with the magnetic field.

18. A method of making a lipid nanodisc, the method comprising:
    contacting:
        a lipid, and
        an acryloyl-based copolymer comprising a first monomer unit having a pendant hydrophobic group and a second monomer unit having a pendant hydrophilic group,
    to form a lipid nanodisc comprising a disc shaped lipid nanoparticle comprising a lipid bilayer comprising a first hydrophilic face and a second hydrophilic face opposing the first hydrophilic face, and a hydrophobic edge between the opposing hydrophilic faces and the copolymer encircling the hydrophobic edge of the lipid bilayer.

19. A method of characterizing a membrane protein, the method comprising:
    contacting the lipid nanodisc of claim 1 with a membrane protein to form a membrane protein-nanodisc comprising the membrane protein spanning across the lipid bilayer from the first hydrophilic face to the second hydrophilic face; and,
    characterizing the lipid nanodisc comprising the membrane protein.

* * * * *